(12) United States Patent
Park (10) Patent No.: US 11,419,669 B2
(45) Date of Patent: Aug. 23, 2022

(54) ELECTROSURGICAL DEVICE HAVING EASILY ADJUSTABLE LENGTH

(71) Applicant: Ik Ro Park, Gangwon-do (KR)

(72) Inventor: Ik Ro Park, Gangwon-do (KR)

( * ) Notice: Subject to any disclaimer, the term of this patent is extended or adjusted under 35 U.S.C. 154(b) by 1025 days.

(21) Appl. No.: 15/755,203

(22) PCT Filed: Jan. 19, 2016

(86) PCT No.: PCT/KR2016/000543
§ 371 (c)(1),
(2) Date: Feb. 26, 2018

(87) PCT Pub. No.: WO2017/099291
PCT Pub. Date: Jun. 15, 2017

(65) Prior Publication Data
US 2018/0243026 A1   Aug. 30, 2018

(30) Foreign Application Priority Data

Dec. 9, 2015   (KR) .......................... 10-2015-0174736

(51) Int. Cl.
*A61B 18/14*   (2006.01)
*A61B 18/00*   (2006.01)
*A61B 17/00*   (2006.01)

(52) U.S. Cl.
CPC ........ *A61B 18/148* (2013.01); *A61B 18/1402* (2013.01); *A61B 2017/00862* (2013.01); *A61B 2017/00991* (2013.01); *A61B 2018/0091* (2013.01); *A61B 2018/00196* (2013.01); *A61B 2018/1412* (2013.01); *A61B 2218/007* (2013.01)

(58) Field of Classification Search
CPC ........ A61B 18/1412; A61B 2018/1412; A61B 2218/007; A61B 2017/00991; A61B 2018/00196; A61B 2018/0091; A61B 18/148; A61B 18/1402
See application file for complete search history.

(56) References Cited

U.S. PATENT DOCUMENTS

| | | | |
|---|---|---|---|
| 6,197,024 B1 * | 3/2001 | Sullivan | A61B 18/1402 606/41 |
| 8,128,622 B2 | 3/2012 | Podhajsky et al. | |
| 2006/0264928 A1 * | 11/2006 | Kornerup | A61B 18/1402 606/45 |
| 2014/0052131 A1 * | 2/2014 | Busch-Madsen | A61B 18/1477 606/41 |
| 2015/0209100 A1 * | 7/2015 | Ineson | A61B 18/1402 606/42 |

FOREIGN PATENT DOCUMENTS

| | | |
|---|---|---|
| KR | 2020110002463 | 3/2011 |
| KR | 1020140144127 | 12/2014 |
| KR | 1020150113556 | 10/2015 |

* cited by examiner

*Primary Examiner* — Jaymi E Della
(74) *Attorney, Agent, or Firm* — Studebaker & Brackett PC (57) ABSTRACT

An electrosurgical device having an easily adjustable length, in which the entire length of the device can be easily adjusted by allowing a stretching member having a blade to be easily moved in a body by unlocking the stretching member in a one-touch button type. Therefore, an operator can easily insert the blade inside incised skin of a patient.

6 Claims, 10 Drawing Sheets

ELECTROSURGICAL DEVICE HAVING EASILY ADJUSTABLE LENGTH

CROSS REFERENCE TO RELATED APPLICATIONS

This application is the National Phase application of International Application No. PCT/KR2016/000543 filed on Jan. 19, 2016, which claims the priority of Korean Patent Application No. 10-2015-0174736, filed on Dec. 9, 2015.

BACKGROUND

The present invention relates to an electrosurgical device having an easily adjustable length and, more particularly to an electrosurgical device of which the entire length can be easily adjusted by allowing a stretching member having a blade to be easily moved in a body in a one-touch button type.

In general, an electrosurgical unit (ESU) is a representative medial instrument that is used to incise a portion of tissues of a human body or coagulate tissues and blood in a surgical operation, using electricity, instead of surgical knives.

The electrosurgical unit, which uses a principle that generates a short spark or heat without applying electric shock or stimulation to a muscle when a high-frequency current flows through a human body, incises a desired tissue of a body, using high-frequency energy of about 100° C. or coagulates a tissue, using high-frequency energy of about 60° C.

However, such electrosurgical units of the related art cannot be adjusted in the entire length, so it is required to prepare several electrosurgical units with blades having different lengths, for example, in order to insert a blade into deep into a human body, depending on the positions to be operated or to use a blade on the surface of a human body.

SUMMARY OF THE INVENTION

In order to solve the problems of the related art, an object of the present invention is to provide an electrosurgical device of which the entire length can be easily adjusted by allowing a stretching member having a blade to be easily moved in a body in a one-touch button type.

In order to achieve the objects, an electrosurgical device having an easily adjustable length includes: a body elongated in a longitudinal direction and having a space longitudinally defined therein; an operation unit having an operation member with a first side disposed in the space and a second side exposed over the space, a substrate disposed in the space and electrically connected with the operation member, and a contact member elongated in the space with a top thereof in electrical contact with the substrate; a stretching member being slidable in the space and having a plurality of locking steps longitudinally formed on a top thereof; a button stopper supported and moved on the body to or not to be locked to the locking steps; a contact guide with a first end disposed in the stretching member and a second end extending toward the contact member; and a blade coupled to the first end of the contact guide and extending out of the stretching member, in which when the stretching member is moved in the space without the button stopper locked to the locking steps, the contact guide slides along the contact member in contact with the contact member.

The button stopper may have a rotation guide rotatably disposed in the space of the body, a button portion extending upward to be exposed over the space at a first side of the rotation guide, and a locking portion extending at a second side of the rotation guide to be locked to the locking steps; and when the button portion is pressed down, the locking portion may be lifted not to be locked to the locking steps, and when the button portion is pressed up, the locking portion may be moved down to be locked to the locking steps.

The electrosurgical device may further include an elastic member supported to face a bottom of the button portion in the space to press up the button portion.

The electrosurgical device may further include an elastic member supported to face a top of the locking portion in the space to press down the locking portion such that the button portion is pressed up.

The elastic member may include any one selected from a plate spring, a coil spring, and a rubber member.

A first guide may protrude upward from the locking portion, a second guide may be formed on an inner side of the body at a position facing the first guide, and the elastic member may be disposed between the first guide and the second guide.

The space may include a first receiving portion disposed over a top plate longitudinally elongated therein and a second receiving portion disposed under the top plate with longitudinal front and rear thereof open; the operation member of the operation unit and the substrate may be disposed in the first receiving portion; the contact member of the operation unit may be elongated in the second receiving portion and electrically connected with the substrate through the top plate; the stretching member may be disposed in the second receiving portion under the contact member to be movable forward out of the second receiving portion or into the second receiving portion, and may have a suction passage longitudinally formed therein; the contact guide may have a first end disposed in the suction passage and a second end extending toward the contact member through the suction passage; the button stopper may be rotatably supported on the top plate with a first side exposed out of the body and a second side disposed to or not to be locked to the locking steps through the top plate; and the blade may be coupled to the first end of the contact guide and may extend out of the suction passage.

The contact guide may have a front end extending toward a front of the suction passage where the blade is disposed, a rear end extending to a rear of the suction passage, and a contact terminal bent toward the contact member at the rear; and the contact terminal may be configured to be in contact with the contact member, so power applied to the contact member may be transmitted to the blade connected with the contact guide.

A cut guide may be formed by cutting forward a rear, where the contact terminal is disposed, of the stretching member, and the contact terminal may be guided in the cut guide.

A coupling guide may be inserted in a front, which faces the blade, of the suction passage, and the blade may be fitted in a first end of the coupling guide, the contact guide may be fitted in a second end of the coupling guide, and the blade and the coupling guide may be electrically connected to each other.

According to the present invention, by unlocking the stretching member in one-touch button type that pressing down the button portion once, the stretching member combined with the blade can be easily moved in the body, and accordingly, the entire length can be easily adjusted. Accordingly, an operator can easily insert the blade through incised skin of a patient.

Further, when the stretching member is unlocked and the entire length is adjusted, the elastic member presses up the button, so the stretching member is naturally locked. Accordingly, an operator does not need to specifically lock the stretching member 300 in complicated operation environments.

REFERENCE NUMERALS

| | |
|---|---|
| 50: Electrosurgical device | 100: Body |
| 110: Upper body | 110a: First receiving portion |
| 111: Operation hole | 112: Button hole |
| 114: Second guide | 120: Lower body |
| 120a: Second receiving portion | 122: Top plate |
| 122a: Projection hole | 124: Button guide |
| 124a: Coupling pivot | 124b: Locking guide |
| 124c: Downward guide | 200: Operation unit |
| 210: Operation member | 220: Substrate |
| 230: Contact member | 232: Contact protrusion |
| 300: Stretching member | 300a: Suction passage |
| 302: Locking step | 304: Cut guide |
| 310: Coupling guide | 312: Coupling portion |
| 400: Button stopper | 402: Rotation guide |
| 404: Locking portion | 405: First guide |
| 406: Button portion | 450, 460: Elastic member |
| 500: Contact guide | 502: Blade coupling portion |
| 504: Contact terminal | 600: Blade |

DETAILED DESCRIPTION OF THE INVENTION

Hereinafter, electrosurgical device having an easily adjustable length according to an embodiment of the present invention is described in detail with reference to the accompanying drawings.

Figure 1:
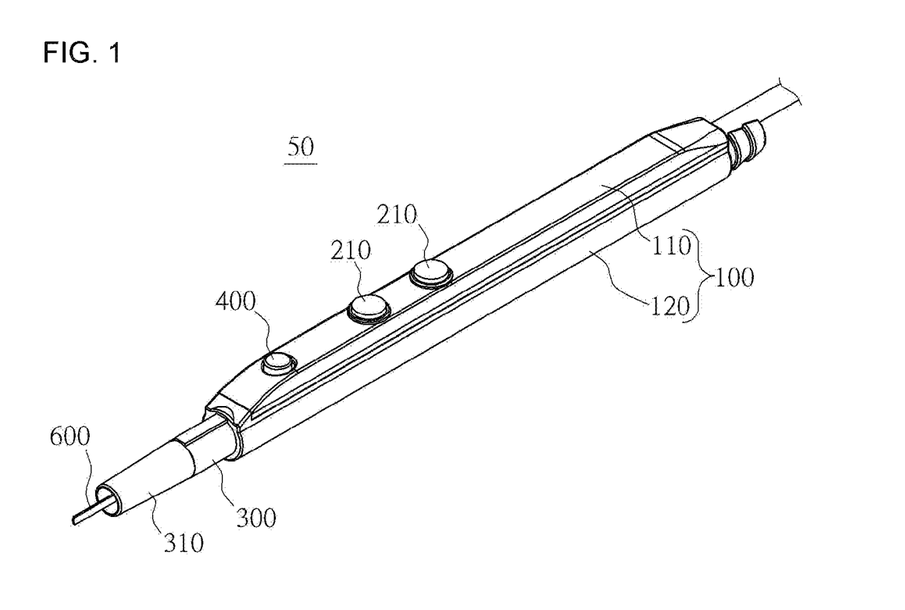
FIG. 1 is a view schematically showing an electrosurgical device having an easily adjustable length according to an embodiment of the present invention.

FIG. 1 is a view schematically showing an electrosurgical device having an easily adjustable length according to an embodiment of the present invention.

Referring to FIG. 1, an electrosurgical device 50 having an easily adjustable length according to an embodiment of the present invention, which is used for an operator such as a doctor to incise or coagulate a portion of a tissue of a human body, includes a body 100, an operation unit 200 (shown in FIG. 2), a stretching member 300, a button stopper 400, a contact guide 500 (shown in FIG. 2), and a blade 600. Unless stated specifically, the direction close to a tissue of a human body is defined as a forward direction and the opposite direction is defined as a backward direction when a user incises or coagulates a tissue of a human body, using the blade 600 with the body 100 in his/her hand. Detailed configurations of the components are described hereafter with reference to FIGS. 2 and 3.

Figure 2:
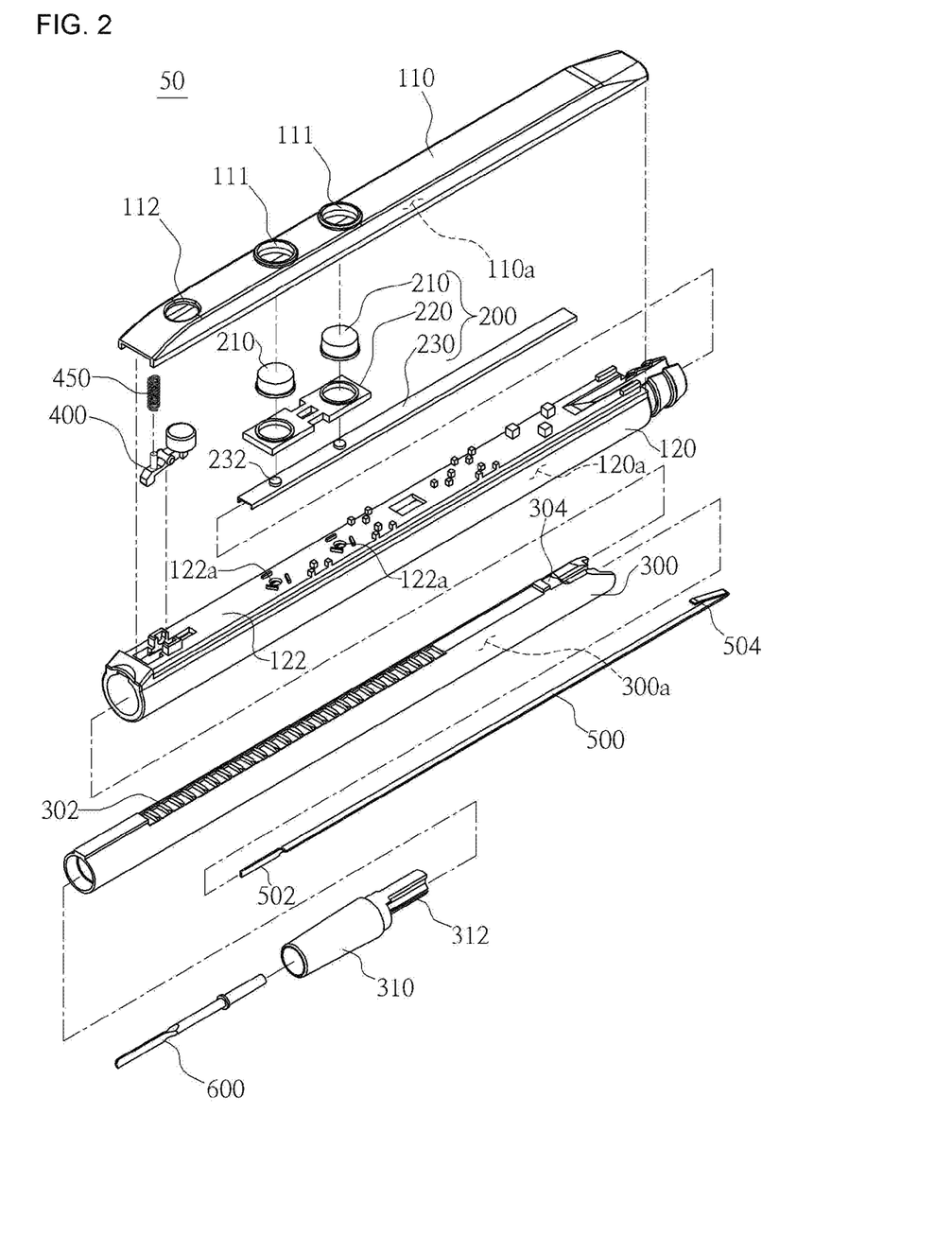
FIG. 2 is an exploded view showing the electrosurgical device having an easily adjustable length according to an embodiment of the present invention.
Figure 3:
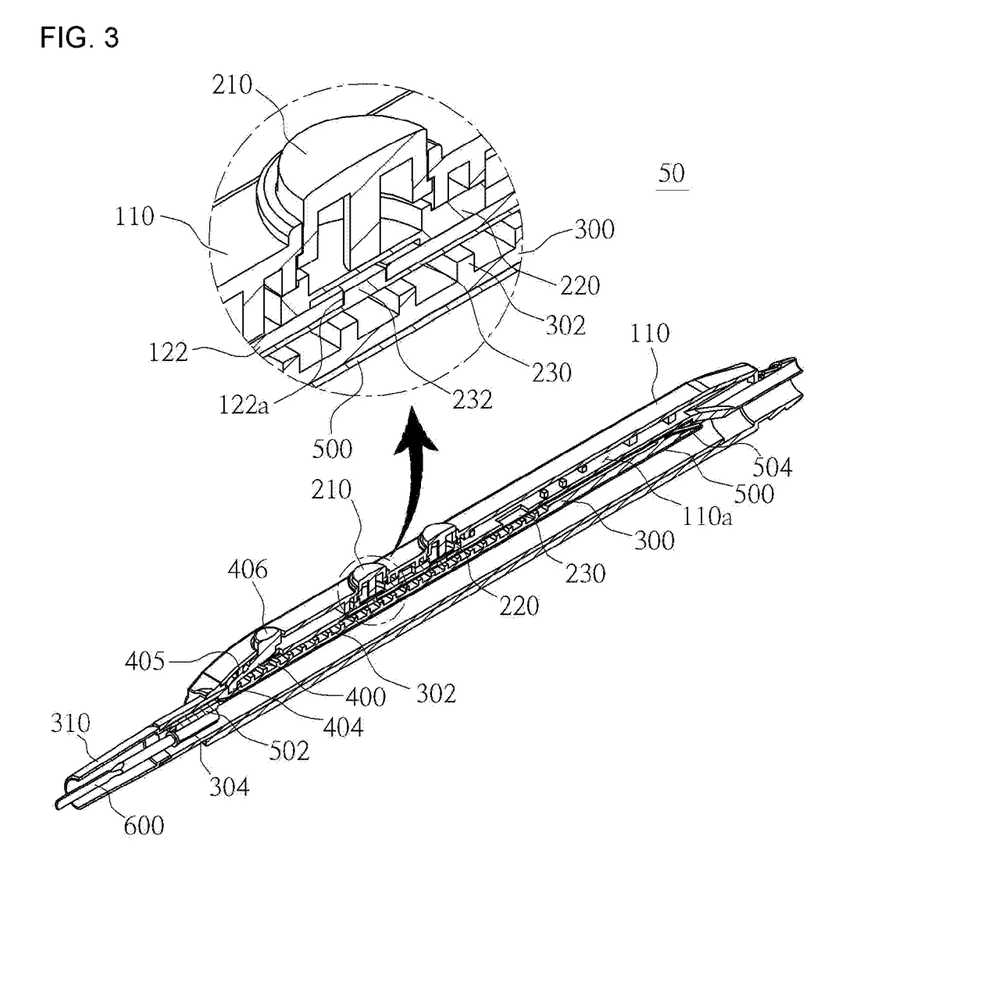
FIG. 3 is a cross-sectional view schematically showing the electrosurgical device having an easily adjustable length according to an embodiment of the present invention.

FIG. 2 is an exploded view showing the electrosurgical device having an easily adjustable length according to an embodiment of the present invention. FIG. 3 is a cross-sectional view schematically showing the electrosurgical device having an easily adjustable length according to an embodiment of the present invention.

Referring to FIGS. 2 and 3, the body 100, which is a part that a user holds with his/her hand, is elongated in a longitudinal direction and has a space longitudinally defined therein. The body 100, for example, may include a lower body 120 longitudinally elongated and an upper body 110 disposed over the lower body 120. In some cases, the upper body 110 and the lower body 120 may be integrated in one unit. The space may have a first receiving portion 110a disposed between a top plate 122 disposed on the top of the lower body 120 and the upper body 110 and a second receiving portion 120a disposed under the top plate 122, that is, in the lower body 120. The second receiving portion 120a may be open at the front and rear longitudinal ends.

The operation unit 200 includes operation members 210, a substrate 220, and a contact member 230. The operation member 210, for example, which may be one or more buttons or touch panels, are disposed at a predetermined distance backward from the front of the first receiving portion 110a, and have tops that are open through the top of the first receiving portion 110a. Operation holes 111 are formed through the upper body 110 at positions corresponding to the operation members 210 and the operation members 210 are exposed through the operation holes 111. The substrate 220 is, for example, a PCB (Printed Circuit Board), is disposed in the first receiving portion 110a to face the operation members 210, and is electrically connected with the operation members 210. Further, the substrate adjusts the amount of high-frequency energy applied from the outside when the operation members 210 are operated, and then transmits the high-frequency energy to the blade 600 to be described below. The contact member 230 is made of a conductive material, is elongated backward along the top of the second receiving portion 120a of the lower body 120, and has contact projections 232 to be electrically connected with the substrate 220 through the top plate 122 disposed on the second receiving portion 120a. Projection holes 122a are formed through the top plate 122 at positions corresponding to the contact projections 232, so the contact projections 232 are electrically connected with the substrate 220 through the projection holes 122a.

The stretching member 300 is inserted in the second receiving portion 120a and positioned under the contact member 230 disposed on the second receiving portion 120a. The stretching member 300 is configured to be able to longitudinally move in the second receiving portion 120a, and has a suction passage 300a longitudinally formed therein and a plurality of locking steps 302 longitudinally formed from the front portion to the rear portion on the top facing the first receiving portion 110a. A coupling guide 310 may be coupled to the front of the suction passage 300a of the stretching member 300 and the rear of the suction passage 300a of the stretching member 300 may be positioned inward further than the rear of the second receiving portion 120a. The coupling guide 310 is formed in a cylindrical shape and has a coupling portion 312 of which both ends are open, at the rear thereof. A suction unit (not shown) having a smoke evacuator is connected to the rear of the second receiving portion 120a to suction air so that smoke that is dispersed around the blade 600 when a user incises or coagulates a portion of a tissue of the body of a patient, using the blade 600, is easily suctioned into the suction passage 300a and the second receiving portion 120a.

The button stopper 400 and the elastic member 450 restrict movement of the stretching member 300 and are described with reference to FIG. 4.

The contact guide 500 is made of a conductive material, is elongated in the longitudinal direction of the suction passage 300a, and has a blade coupling portion 502 at the longitudinal front end and a contact terminal 504 bending toward the contact member through the suction passage 300a, at the longitudinal rear end thereof. The blade coupling portion 502 is inserted and fixed in the rear portion of the coupling portion 312 of the coupling guide 310.

The blade 600 is longitudinally elongated with an end inserted in the front portion of the coupling portion 312 of the coupling guide 310 and electrically connected with the blade coupling portion 502 of the contact guide 500 and the other end extending into the front portion of the suction passage 300a. High-frequency energy applied to the substrate 200 from the outside is transmitted to the blade 600 through the contact member 230 and the contact guide 500, so a portion of the tissue of the patient's body is incised or coagulated by the high-frequency energy.

Figure 4:
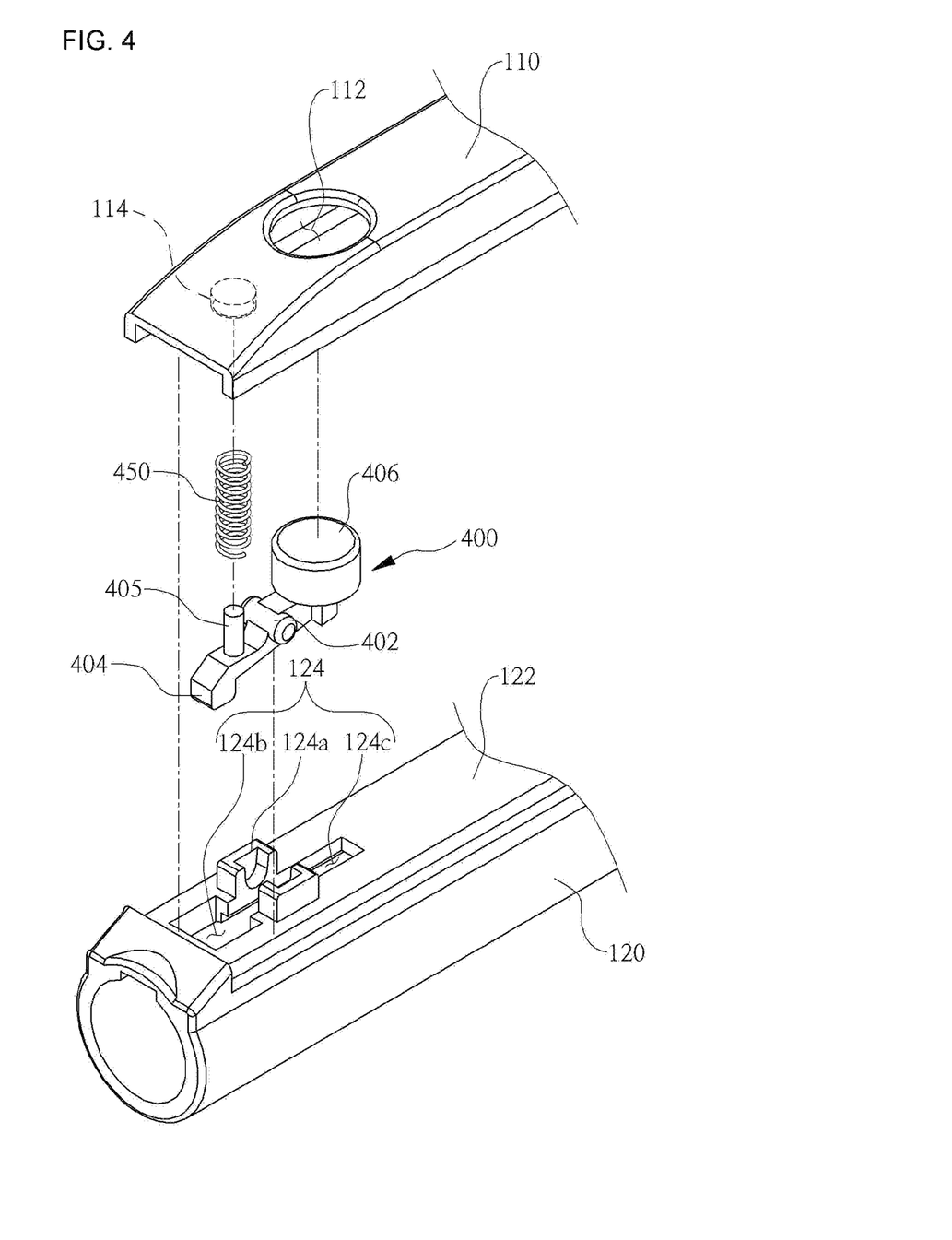
FIG. 4 is view showing a button stopper and an elastic member combined with a body of the electrosurgical device having an easily adjustable length according to an embodiment of the present invention.
Figure 5:
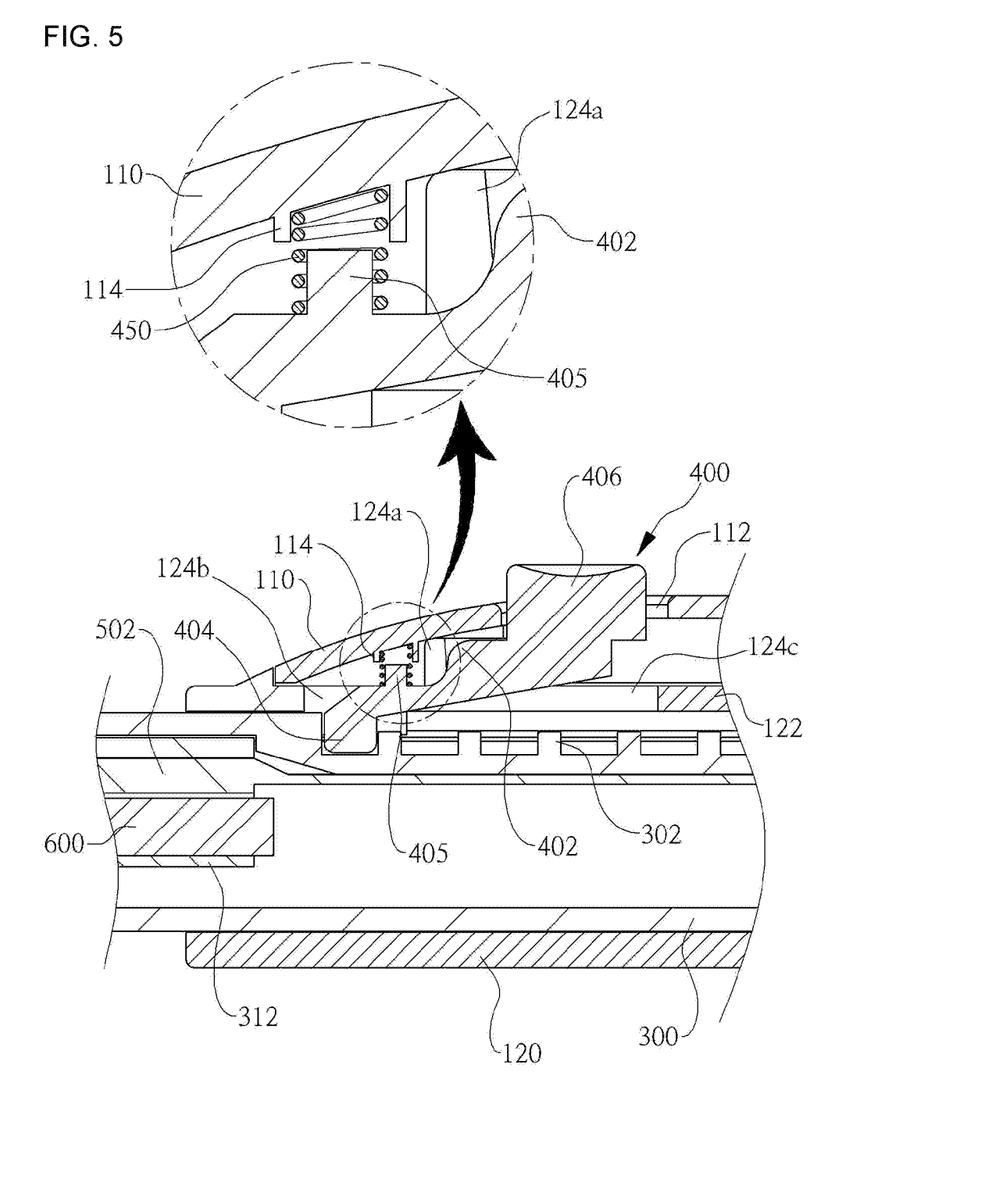
FIG. 5 is a cross-sectional view showing the button stopper and the elastic member combined with the body of the electrosurgical device having an easily adjustable length according to an embodiment of the present invention.

FIG. 4 is view showing the button stopper and the elastic member combined with a body of the electrosurgical device having an easily adjustable length according to an embodiment of the present invention. FIG. 5 is a cross-sectional view showing the button stopper and the elastic member combined with the body of the electrosurgical device having an easily adjustable length according to an embodiment of the present invention.

Referring to FIGS. 4 and 5, the button stopper 400, which is rotated on the body 100 to or not to be locked to the locking steps 302, has a rotation guide 402 rotatably disposed on the top plate 122 of the lower body 120, a locking portion 404 extending from the longitudinal front of the rotation guide 402 to be locked to the locking steps 302, and a button portion 406 extending upward to be exposed from the longitudinal rear of the rotation guide 402. A first guide 405 protrudes upward from the locking portion 404 and a second guide 114 protrudes from the inner side of the upper body 110 to face the first guide 405. The second guide 114 is formed in a ring shape. The elastic member 450 to be described below is fitted between the first guide 405 and the second guide 114.

The elastic member 450, which presses upward the button portion 406 by applying downward to the locking portion 404 of the button stopper 400, may include a plate spring, a coil spring, and a rubber member. The elastic member 450 is fitted between the first guide 405 and the second guide 114, whereby it is supported by the first guide 405 and pressed downward the locking portion 404 connected with the second guide 114.

A button hole 112 is formed at the position corresponding to the button portion 406 of the upper body 110, so the button portion 406 is exposed to the outside through the button hole 112. A button guide 124 is formed on the top plate 122 of the lower body 120 at a position corresponding to the button stopper 400. The button guide 124 has a coupling pivot 124a in which the rotation guide 402 is rotatably inserted, a locking guide 124b formed through the top plate at the front of the coupling pivot 124a such that the locking portion 404 is inserted in the second receiving portion 120a of the lower body 120, and a downward guide 124c formed through the top plate at the rear of the coupling pivot 124a such that the rear of the rotation guide 402 is inserted in the second receiving portion 120a. When the button 406 is pressed down, the locking portion 404 is lifted not to be locked to the locking steps 302. Further, when the button portion 406 is pressed up, the locking portion 404 is moved down and locked to the locking steps 302. When the locking portion 404 of the button stopper 400 is locked to the locking steps 302, the stretching member 300 is locked and restricted in movement.

As described above, when the button portion 406 is pressed down, the locking portion 404 is not locked to the locking steps 302, so the stretching member 300 is unlocked. Further, as the stretching member 300 is unlocked, the stretching member 300 is moved in the lower body 120, so the entire length is adjusted. Further, when the entire length is adjusted, the elastic member 450 presses up the button portion 406 and the stretching member 300 is naturally locked. Accordingly, an operator does not need to specifically lock the stretching member 300 in complicated operation environments.

Figure 6:
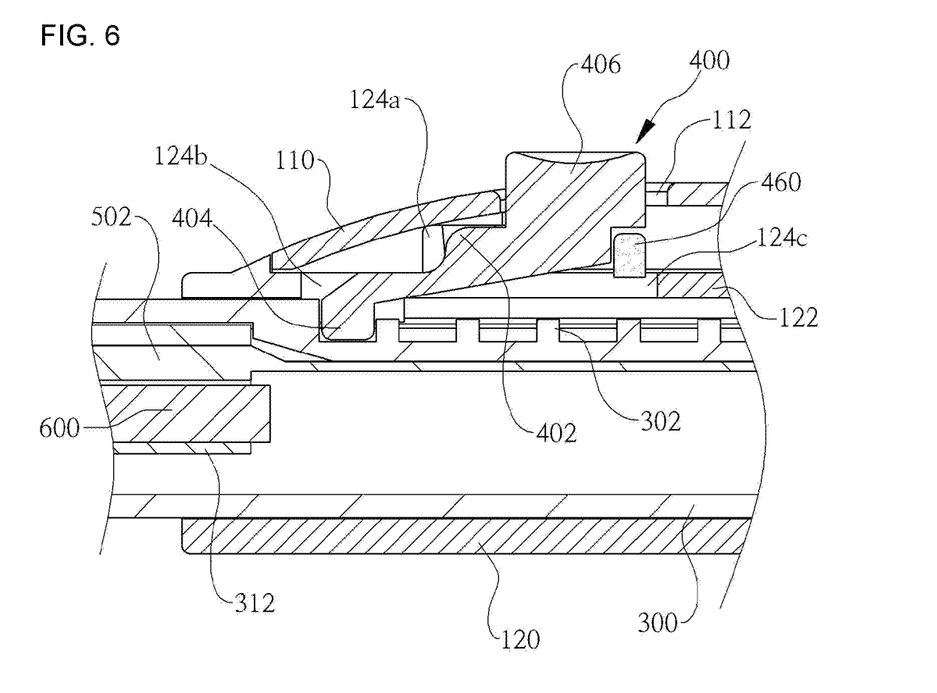
FIG. 6 is a view showing another example of the button stopper and the elastic member combined with the body of the electrosurgical device having an easily adjustable length according to an embodiment of the present invention.

FIG. 6 is a view showing another example of the button stopper and the elastic member combined with the body of the electrosurgical device having an easily adjustable length according to an embodiment of the present invention.

Referring to FIG. 6, an elastic member 460 may be disposed under the button portion 406. In this case, the elastic member 460 is supported on the top plate 122 disposed under the button portion 406 and presses up the button portion 406. The elastic member 460 may include a plate spring, a coil spring, or a rubber member.

Figure 7:
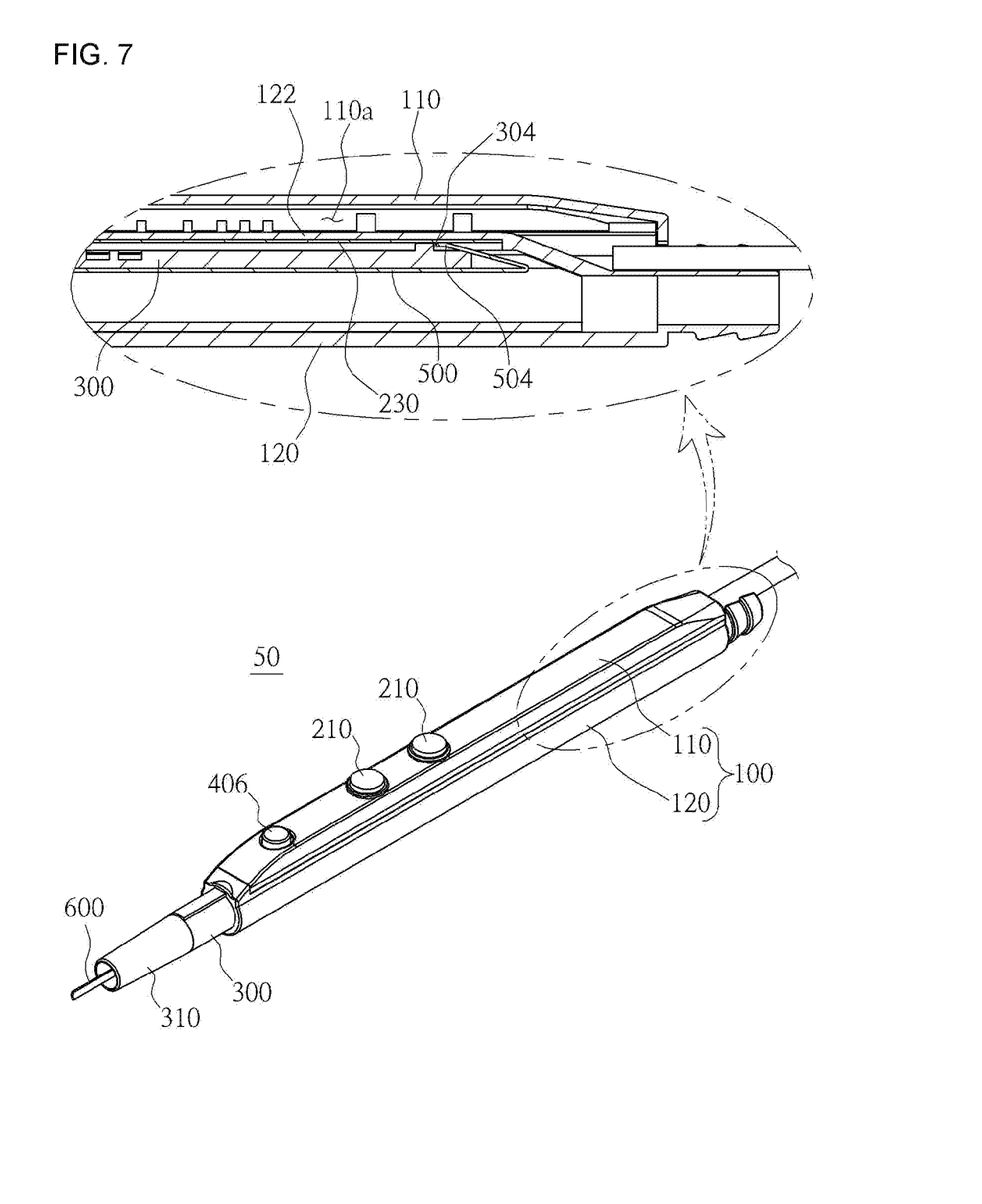
FIG. 7 is a view showing a contact member and a contact guide that are in contact with each other in the electrosurgical device having an easily adjustable length according to an embodiment of the present invention.

FIG. 7 is a view showing the contact member and the contact guide that are in contact with each other in the electrosurgical device having an easily adjustable length according to an embodiment of the present invention.

Referring to FIG. 7, a cut guide 304 is elongated toward the front of the stretching member 300 at the rear portion of the stretching member 300. The contact member 230 is elongated to cover the cut guide 304. The contact terminal 504 of the contact guide 500 is bent toward the cut guide 304 to be in contact with the contact member 230 through the cut guide 304.

When the stretching member 300 is moved forward or backward in this state, the contact terminal 504 of the contact guide 500 connected with the stretching member 300 is also moved forward or backward, in which the contact terminal 504 is moved forward or backward in contact with the contact member 230 disposed on the stretching member 300.

Accordingly, high-frequency energy applied to the substrate 220 is easily transmitted to the blade 600 to be described below through the contact member 230 and the contact guide 500.

Figure 8:
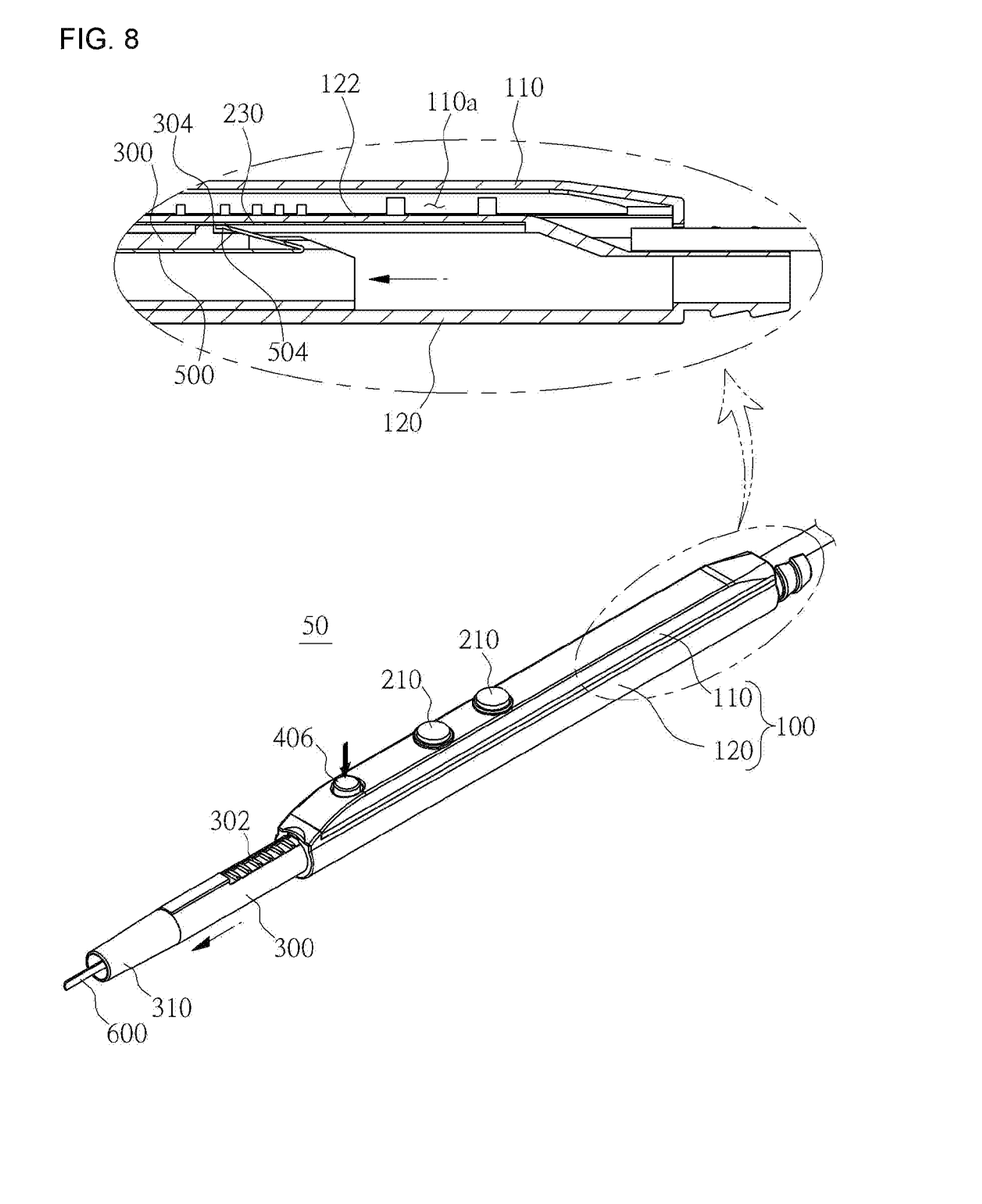
FIG. 8 is a view showing forward movement of the stretching member in the electrosurgical device having an easily adjustable length according to an embodiment of the present invention.

FIG. 8 is a view showing forward movement of the stretching member in the electrosurgical device having an easily adjustable length according to an embodiment of the present invention.

Referring to FIG. 8, according to the electrosurgical device 50 having an easily adjustable length, when the button portion 406 of the button stopper 400 is pressed down, the locking portion 404 of the button stopper 400 is lifted and the stretching member 300 is unlocked. In this process, the stretching member 300 is moved forward or backward in the second receiving portion 120*a*, so the entire length is easily adjusted.

Figure 9:
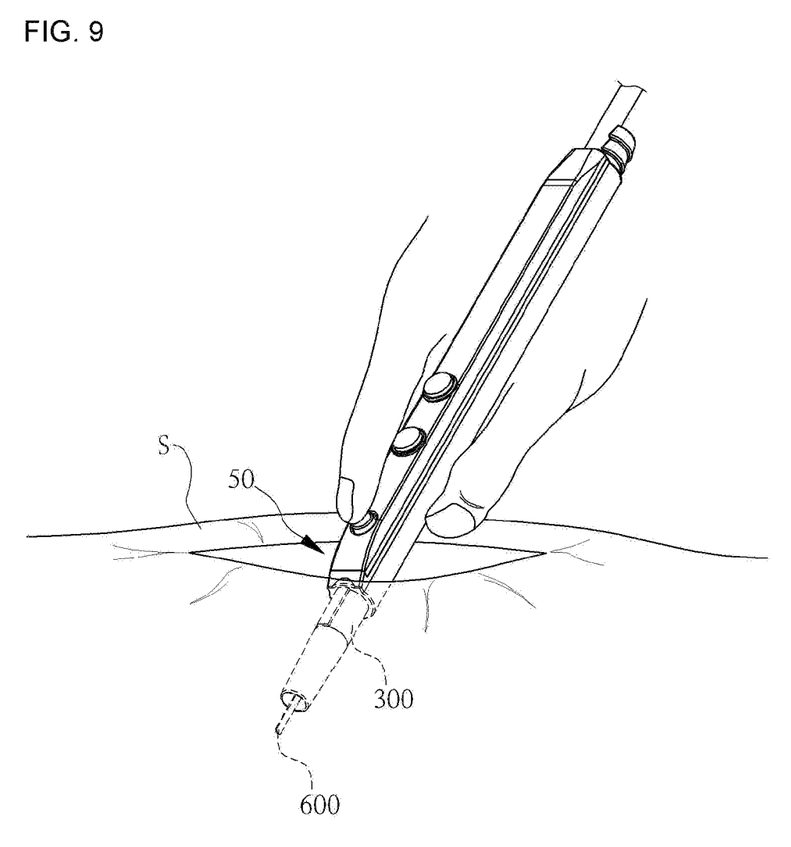
FIGS. 9 and 10 are views schematically showing a difference in insertion depth in a skin tissue, depending on the position of the stretching member in the electrosurgical device having an easily adjustable length according to an embodiment of the present invention.
Figure 10:
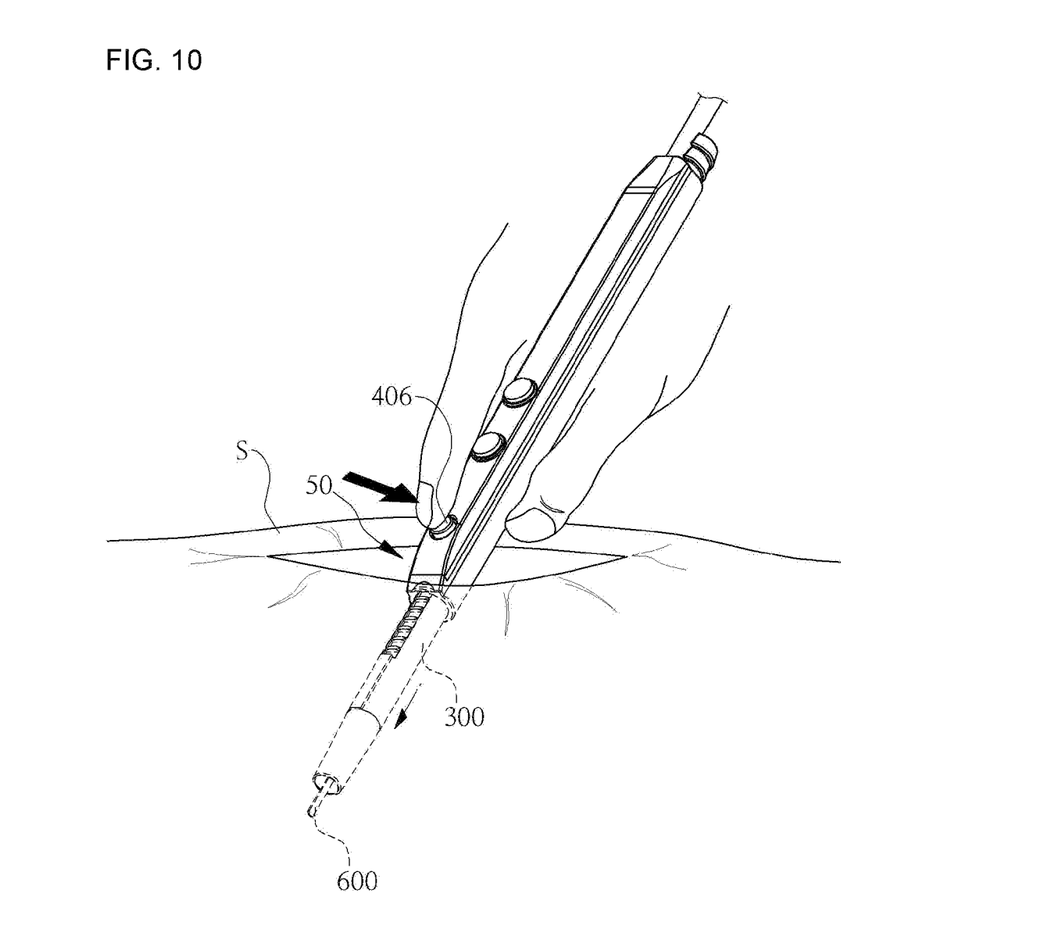

FIGS. 9 and 10 are views schematically showing a difference in insertion depth in a skin tissue, depending on the position of the stretching unit in the electrosurgical device having an easily adjustable length according to an embodiment of the present invention.

Referring to FIG. 9 first, an operator holds the body 100 and inserts the blade 600 through incised skin S. In this process, since the stretching member 300 has been moved backward, the lengths of the body 100 and the blade 600 is too small, so the blade 600 cannot be pushed deep into the incised skin S.

Next, referring to FIG. 10, the operator holding the body 100 moves the stretching member 300 forward in the second receiving portion 120*a* by pressing down the button portion 406 of the button stopper 400. In this process, the operator holds with his/her hand and moves forward the stretching member 300. Accordingly, the blade 600 is moved forward together with the stretching member 300. Then, when the operator takes the hand off the button portion 406 of the button stopper 400, the locking portion 404 of the button stopper 400 is locked to the locking steps 302 of the stretching member 300, whereby the stretching member 300 is naturally locked.

As described above, by unlocking the stretching member 300 in one-touch button type that pressing down the button portion 406 once, the stretching member 300 combined with the blade 600 can be easily moved in the body 100, and accordingly, the entire length can be easily adjusted. Accordingly, an operator can easily insert the blade 600 through incised skin of a patient.

Although the present invention was described in detail with reference to the embodiment, the present invention is not limited to the embodiment, it is apparent to those skilled in the art that the present invention may be changed and modified in various ways within the scope of the present invention, and if the changes and modifications are included in the following claims, the spirits of the changes and modifications should be construed as being included in the present invention.

The invention claimed is:

1. An electrosurgical device having an easily adjustable length, the electrosurgical device comprising:
   a body elongated in a longitudinal direction and having a space longitudinally defined therein;
   an operation unit having an operation member with a first side disposed in the space and a second side exposed over the space, a substrate disposed in the space and electrically connected with the operation member, and a contact member elongated in the space with a top thereof in electrical contact with the substrate;
   a stretching member being slidable in the space and having a plurality of locking steps longitudinally formed on a top thereof;
   a button stopper supported and moved on the body to be or not to be locked to one of the plurality of locking steps;
   a contact guide with a first end disposed in the stretching member and a second end extending toward the contact member;
   a blade coupled to the first end of the contact guide and extending out of the stretching member,
   wherein, when the stretching member is moved in the space without the button stopper locked to any one of the plurality of locking steps, the contact guide slides along the contact member in contact with the contact member,
   wherein the button stopper has a rotation guide rotatably disposed in the space of the body, a button portion extending upward to be exposed over the space at a first side of the rotation guide, and a locking portion extending at a second side of the rotation guide to be locked to the plurality of locking steps,
   wherein, when the button portion is pressed down, the locking portion is lifted not to be locked to the any one of the plurality of locking steps, and when the button portion is pressed up, the locking portion is moved down to be locked to the one of the plurality of locking steps;
   an elastic member supported to face a top of the locking portion in the space to press down the locking portion such that the button portion is pressed up;
   a first guide that has a cylinder-shape and protrudes upward from the locking portion, wherein a lower portion of the elastic member winds the first guide; and
   a second guide formed on an inner side of the body at a position facing the first guide, wherein an upper portion of the elastic member is positioned inside the second guide, and
   wherein an upper portion of the first guide is configured to be inserted into inside the second guide when the button portion is pressed down.

2. The electrosurgical device of claim 1, wherein the space includes a first receiving portion disposed over a top plate longitudinally elongated therein and a second receiving portion disposed under the top plate with longitudinal front and rear thereof open,
   the operation member of the operation unit and the substrate are disposed in the first receiving portion, the contact member of the operation unit is elongated in the second receiving portion and electrically connected with the substrate through the top plate,
   the stretching member is disposed in the second receiving portion under the contact member to be movable forward out of the second receiving portion or into the second receiving portion, and has a suction passage longitudinally formed therein,
   the contact guide has a first end disposed in the suction passage and a second end extending toward the contact member through the suction passage,
   the button stopper is rotatably supported on the top plate with a first side exposed out of the body and a second side disposed to be or not to be locked to the plurality of locking steps through the top plate, and the blade is coupled to the first end of the contact guide and extends out of the suction passage.

3. The electro surgical device of claim 2, wherein the contact guide has a front end extending toward a front of the suction passage where the blade is disposed, a rear end extending to a rear of the suction passage, and a contact terminal bent toward the contact member at the rear, and the contact terminal is configured to be in contact with the contact member, so power applied to the contact member is transmitted to the blade connected with the contact guide.

4. The electrosurgical device of claim 3, wherein a cut guide is formed by cutting forward a rear, where the contact terminal is disposed, of the stretching member, and the contact terminal is guided in the cut guide.

5. The electrosurgical device of claim 2, wherein a coupling guide is inserted in a front, which faces the blade, of the suction passage, and the blade is fitted in a first end of the coupling guide, the contact guide is fitted in a second end of the coupling guide, and the blade and the coupling guide are electrically connected to each other.

6. The electrosurgical device of claim 1, wherein the elastic member includes any one selected from a plate spring, a coil spring, or a rubber member.

\* \* \* \* \*